United States Patent [19]
Harimaya et al.

[11] Patent Number: 5,817,816
[45] Date of Patent: Oct. 6, 1998

[54] SESQUITERPENE DERIVATIVES HAVING PROGESTERONE RECEPTOR BINDING INHIBITORY ACTIVITY

[75] Inventors: Kenzo Harimaya; Emiko Magome; Yuji Tabata; Toru Sasaki, all of Yokohama, Japan

[73] Assignee: Meiji Seika Kaisha, Ltd., Tokyo-to, Japan

[21] Appl. No.: 878,841

[22] Filed: Jun. 19, 1997

[51] Int. Cl.[6] ......................... A61K 31/365; C07D 307/92
[52] U.S. Cl. ............................................. 514/468; 549/299
[58] Field of Search ............................... 514/468; 549/299

[56] References Cited

U.S. PATENT DOCUMENTS

| | | | |
|---|---|---|---|
| 5,663,196 | 9/1997 | Sari et al. ................................. | 514/468 |
| 5,712,306 | 1/1998 | Tabata et al. ............................ | 514/468 |

OTHER PUBLICATIONS

F. Bohlmann et al., *Phytochemistry*, 17 (7), 1173–1178 (1978).

*Primary Examiner*—Jane Fan
*Attorney, Agent, or Firm*—Wenderoth, Lind & Ponack, L.L.P.

[57] ABSTRACT

Sesquiterpene derivatives, represented by the following formulae (I) and (II), having progesterone receptor binding inhibitory activity are disclosed. They can be used as therapeutic and prophylactic agents for progesterone-related diseases, for example, as a carcinostatic agent for breast cancer or ovarian cancer, a therapeutic agent for hysteromyoma, endometriosis, meningioma, or myeloma, an abortifacient, an oral contraceptive pill, or a therapeutic or prophylactic agent for osteoporosis or climacteric disturbance. These compounds have no steroid skeleton and, hence, are considered to be advantageously free from side effect inherent in steroid such as found in conventional progesterone receptor binding inhibitors having a steroid skeleton.

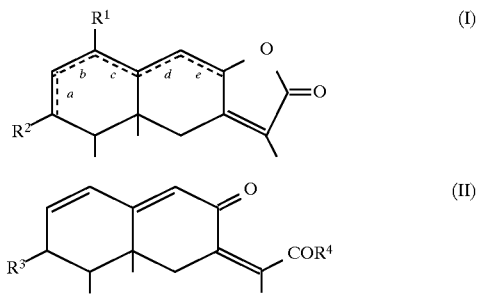

wherein $R^1$ represents a hydrogen atom, a halogen atom, $C_1$–$C_5$ alkoxy, or phenylthio; $R^2$ represents $C_1$–$C_5$ alkoxy or $C_2$–$C_5$ alkanoyloxy; and ---- with letters a, b, c, d, and e attached thereto represent a double bond or a single bond; $R^3$ has the same meaning as $R^2$; and $R^4$ represents $C_1$–$C_5$ alkoxy.

7 Claims, No Drawings

SESQUITERPENE DERIVATIVES HAVING PROGESTERONE RECEPTOR BINDING INHIBITORY ACTIVITY

BACKGROUND OF THE INVENTION

1. Field of Invention

The present invention relates to novel sesquiterpene derivatives as a progesterone receptor binding inhibitor or salts thereof and use of these compounds as pharmaceuticals.

2. Background Art

Surgical endocrinotherapies for breast cancer include ovariectomy (1896), adrenalectomy (1953), and hypophysectomy (1953) which are effective as therapies for breast cancer in progress. These therapies, however, involve removal of an organ involved in the secretion of estrogen and, hence, results in loss of not only estrogen but also steroid hormones, adversely affecting patients.

Non-steroidal anti-estrogen agents such as Tamoxifen, by virtue of low side effect and high effect against breast cancer, have become extensively applied in clinical investigations since the 1970s and replaced the surgical endocrinotherapy used as main therapy for breast cancer up to that point.

More recently, agents having a new mechanism of action, such as aromatase inhibitor, LH-RH (luteinizing hormone releasing hormone) agonist, and progesterone receptor antagonist have been developed.

Antiprogesterone agents under development, such as Mifepristone (RU38486) (FR2497807), Onapristone (ZK98299) (DE3321826), have a steroidal skeleton and, hence, leads to a fear of side effect characteristic of steroid.

Therefore, development of antiprogesterone agents having a nonsteroid skeleton has been strongly desired from the viewpoint of avoiding the problem of side effect.

Some of the present inventors have previously succeeded in isolation of substance PF1092, with an eremophilane skeleton, having inhibitory activity against binding of progesterone to progesterone receptor, from a cultured mixture of fungi belonging to the genus Penicillium (Japanese Patent Laid-Open No. 253467/1996 and EP-A-0722940. Further, various derivatives of substance PF1092 have been synthesized and found to have inhibitory activity against binding of progesterone to progesterone receptor (PCT/JP97/00451, not laid open to public inspection).

SUMMARY OF THE INVENTION

The present inventors have now succeeded in synthesis of novel sesquiterpene derivatives and confirmed that these derivatives have progesterone receptor binding inhibitory activity. The present invention is based on such novel finding.

Accordingly, an object of the present invention is to provide a novel compound as a progesterone receptor binding inhibitor.

Another object of the present invention is to provide a pharmaceutical composition comprising the novel compound as an active ingredient, especially a therapeutic or prophylactic agent for progesterone-related diseases.

A further object of the present invention is to provide an intermediate useful for the synthesis of the novel compound.

The novel compound as a progesterone receptor binding inhibitor according to the first aspect of the present invention is a compound represented by the following formula (I):

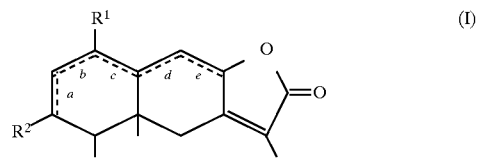

wherein
$R^1$ represents a hydrogen atom, a halogen atom, $C_1$–$C_5$ alkoxy, or phenylthio;
$R^2$ represents $C_1$–$C_5$ alkoxy or $C_2$–$C_5$ alkanoyloxy; and
---- with letters a, b, c, d, and e attached thereto are such that when b and d represent a double bond, a, c, and e represent a single bond; when b and d represent a single bond, a represents a single bond or a double bond with c and e representing a double bond where, when a represents a double bond, both $R^1$ and $R^2$ represent a hydrogen atom.

The novel compound as a progesterone receptor binding inhibitor according to the second aspect of the present invention is a compound represented by the following formula (II):

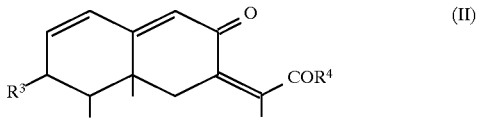

wherein
$R^3$ is as defined for $R^2$ in formula (I) above; and
$R^4$ represents $C_1$–$C_5$ alkoxy.

The intermediate useful for the synthesis of the compounds represented by the formulae (I) and (II) according to the present invention is a compound represented by the following formula (III):

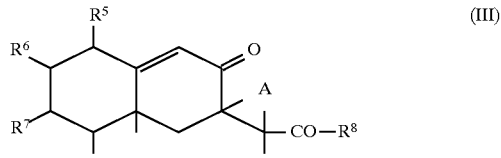

wherein
$R^5$ is as defined for $R^1$ in formula (I);
$R^6$ represents a hydroxyl group or
$R^5$ and $R^6$ combine with each other to form oxo (=O);
$R^7$ is as defined for $R^2$ in the formula (I) above; and
A represents an oxygen atom or a bond for forming a double bond between two carbon atoms with A bonded thereto.

DETAILED DESCRIPTION OF THE INVENTION

Definition

The term "halogen atom" used herein means a fluorine, chlorine, bromine, or iodine atom. Further, the term "alkyl" as a part of a group means a straight-chain or branched alkyl.

Compounds represented by formula (I)

In the formula (I), ---- with letters a, b, c, d, and e attached thereto represent a double bond or a single bond. Consequently, the compounds represented by the formula (I) include: a first group of compounds wherein b and d represent a double bond and a, c, and e represent a single bond; a second group of compounds wherein b and d represent a single bond, a represents a double bond and c and e represent a double bond; and a third group of compounds wherein b and d represent a single bond, a represents a single bond and c and e represent a double bond. In the second group of compounds, both $R^1$ and $R^2$ represent a hydrogen atom. In the first group of compounds, $R^1$ represents preferably a hydrogen atom.

In the formula (I), the $C_1$–$C_5$ alkoxy represented by $R^1$ is preferably $C_1$–$C_3$ alkoxy with methoxy being more preferred.

Since the compounds represented by the formula (I) according to the present invention have several asymmetric carbons, various isomers attributable to these carbons are considered. The present invention embraces these individual isomers and mixtures thereof. The configuration of the compound of the formula (I) may depend on the selection of a starting material and synthesys rute of the compound. Preferred compounds of the formula (I) have a configuration represented by the following formula:

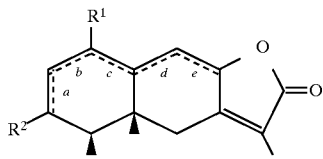

The $C_1$–$C_5$ alkoxy represented by $R^2$ is preferably $C_1$–$C_3$ alkoxy with methoxy being more preferred.

The $C_2$–$C_5$ alkanoyloxy represented by $R^2$ is preferably $C_2$–$C_3$ alkanoyloxy with acetyloxy being more preferred.

Specific examples of preferred compounds represented by the formula (I) include:

3β-acetoxy-1-chloroeremophila-1(10),7(11),8(9)-trien-12,8-olide;

3β-acetoxyeremophila-1(10),7(11),8(9)-trien-12,8-olide

3β-acetoxyeremophila-1(2),7(11),9(10)-trien-12,8β-olide;

eremophila-1(10),2(3),7(11),8(9)-tetraen-12,8-olide

3β-acetoxy-1-thiophenyleremophila-1(10),7(11),8(9)-trien-12,8-olide; and

3β-acetoxy-1-ethoxyeremophila-1(10),7(11),8(9)-trien-12,8-olide.

The compounds represented by the formula (I) may be present in the form of a salt. Examples of the salt include pharmacologically acceptable salts, and specific examples thereof include lithium, sodium, potassium, magnesium, and calcium salts; salts with ammonium and suitable non-toxic amines, for example, $C_1$–$C_6$ alkylamine (for example, triethylamine) salts, $C_1$–$C_6$ alkanolamine (for example, diethanolamine or triethanolamine) salts, procaine salts, cyclohexylamine (for example, dicyclohexylamine) salts, benzylamine (for example, N-methylbenzylamine, N-ethylbenzylamine, N-benzyl-β-phenethylamine, N,N-dibenzylethylenediamine, or dibenzylamine) salts, and heterocyclic amines (for example, morpholine or N-ethylpyridine) salts; salts of hydrohalogenic acids such as hydrofluoric acid, hydrochloric acid, hydrobromic acid and hydroiodic acid; inorganic acid salts such as sulfate, nitrate, phosphate, perchlorate and carbonate; salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid and malic acid; salts of amino acids such as arginic acid, aspartic acid and glutamic acid; and salts of organic acids such as methanesulfonic acid and p-toluenesulfonic acid.

Compounds represented by formula (II)

In the formula (II), $R^3$ is as defined for $R^2$ in formula (I) above, and preferred examples thereof may be the same as described in connection with $R^2$.

In the formula (II), the $C_1$–$C_5$ alkoxy represented by $R^4$ is preferably $C_1$–$C_3$ alkoxy with methoxy being more preferred.

Since the compounds represented by the formula (II) according to the present invention also have several asymmetric carbons, various isomers attributable to these carbons are considered. The present invention embraces these individual isomers and mixtures thereof. The configuration of the compound of the formula (II) may depend on the selection of a starting material and synthesys rute of the compound. Preferred compounds of the formula (II) have a configuration represented by the following formula:

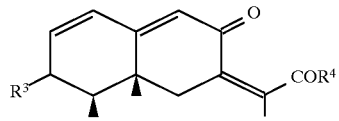

Specific examples of the compounds represented by the formula (II) include 3β-acetoxy-8-oxoeremophila-1(2),7(11),9(10)-trien-12-oic acid methyl ester.

As with the compounds represented by the formula (I), the compounds represented by the formula (II) also may be present in the form of a salt. Specific examples of preferred salts thereof may be the same as those described in connection with the formula (I).

Use of compounds represented by formulae (I) and (II)/pharmaceutical composition The compounds represented by the formulae (I) and (II) have progesterone receptor binding inhibitory activity and, hence, can be used as therapeutic and prophylactic agents for progesterone-related diseases. The progesterone receptor has been reported to be expressed in breast, uterus, ovary, bone, central nerve and the like. Therefore, the compounds represented by the formulae (I) and (II) according to the present invention are useful as therapeutic and prophylactic agents for progesterone-related diseases in these organs. More specifically, they are useful as a carcinostatic agent for breast cancer or ovarian cancer, a therapeutic agent for hysteromyoma, endometriosis, meningioma, or myeloma, an abortifacient, an oral contraceptive pill, or a therapeutic or prophylactic agent for osteoporosis or climacteric disturbance. In particular, the compounds according to the present invention have no steroid skeleton and, hence, are considered to be advantageously free from side effect inherent in steroid such as found in conventional progesterone receptor binding inhibitors having a steroid skeleton.

A pharmaceutical composition comprising as an active ingredient a compound of the present invention can be administered either orally or parenterally (e.g., intravenous injection, intramuscular injection, subcutaneous administration, rectal administration, percutaneous administration) to humans or animals other than humans.

The pharmaceutical composition comprising as an active ingredient a compound of the present invention may be made into a preparation suitable for an administration route to be adopted. Specifically, it may be made into any of the following preparations: an injection for intravenous or intramuscular injection; a capsule, a tablet, a granule, a powder, a pill, fine subtilaes, or a troche for oral administration; a preparation for rectal administration; an oleaginous suppository; and an aqueous suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like.

Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose, carboxymethyl cellulose or a salt thereof, gum arabic, polyethylene glycol, syrup, vaseline, glycerin, ethanol, propylene glycol, citric acid, sodium chloride, sodium sulfite and sodium phosphate.

The dosage of the compound of the present invention may be properly determined in consideration of the symptom and the age and sex of a patient for each case. Regarding the therapeutic or prophylactic agent, especially as a contraceptive or a therapeutic agent for breast cancer or ovarian cancer, however, for intravenous administration, about 0.01 to 1000 mg, preferably 0.1 to 100 mg of the compound is generally administered per day for adult human either at one time or dividedly several times. For intramuscular administration, about 0.01 to 1000 mg, preferably 0.1 to 100 mg of the compound is generally administered per day for adult human either at one time or dividedly several times. For oral administration, about 0.5 to 2000 mg, preferably 1 to 1000 mg of the compound is generally administered per day for adult human either at one time or dividedly several times.

Preparation of compounds represented by formulae (I) and (II) and compound, represented by formula (III), as intermediate for these compounds Preferably, the compounds represented by the formulae (I) and (II) may be prepared from the following PR Toxin (in the following scheme, $R^7$ represents acetyloxy) or a derivative thereof as a starting compound through the compound represented by the formula (III).

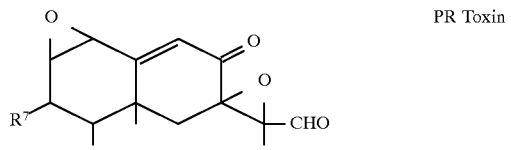

PR Toxin

At the outset, PR Toxin as the starting material is known in the art and is described, for example, in R. D. Wei, P. E. Still, E. B. Smalley, H. K. Schnoses and F. M. Strong, Appl. Microbiol., 25, 111 (1973), and R. D. Wei, H. K. Schnoses, P. A. Hart, and F. M. Strong, Tetrahedron, 31, 109 (1975).

The compound represented by the formula (III) wherein $R^7$ represents alkoxy may be prepared by deacetylating PR Toxin, i.e., a compound wherein $R^7$ represents acetyloxy, and acylating the deacetylated compound. More specifically, deacetylation may be carried out by adding an aqueous strong alkali (for example, 5 to 20% potassium hydroxide or sodium hydroxide) solution in excess to PR Toxin in a solvent (for example, THF or dioxane) and allowing a reaction to proceed at room temperature or heating at 40° to 80° C. for 5 to 20 hr. Subsequent acylation may be carried out by adding a corresponding acid anhydride or acid halide in excess to the deacetylated compound in the presence of a base (for example, dimethylaminopyridine) in a solvent (for example, dichloromethane, pyridine) and allowing a reaction to proceed at room temperature or heating at 40° to 80° C. for 5 to 20 hr.

Further, the compounds represented by the formulae (I) and (II) according to the present invention may be prepared by a process represented by the following scheme 1.

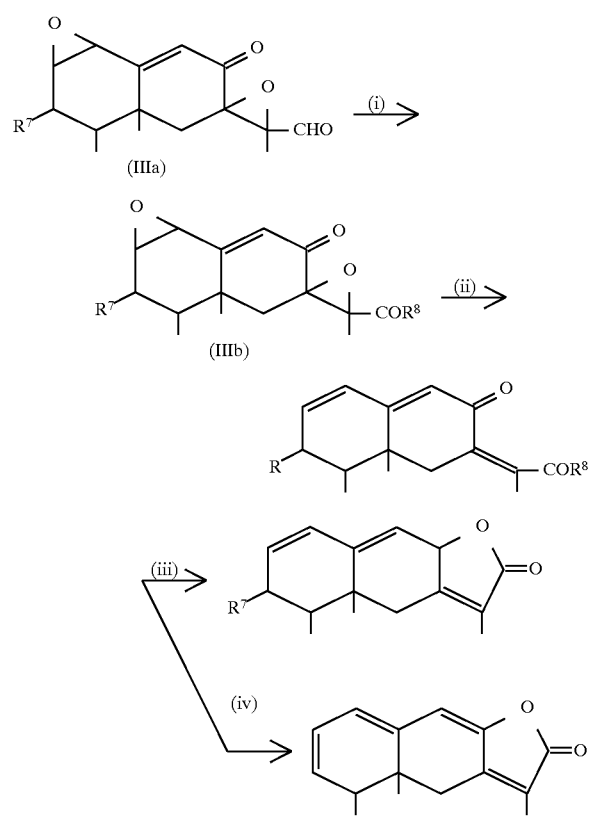

In the step (i), the aldehyde group of the compound represented by the formula (IIIa) is oxidized and then esterified to give a compound represented by the formula (IIIb). In particular, the compound of formula (IIIa) is oxidized with 1.5 to 5 equivalents of sodium chlorite as an oxidizing agent in a solvent (for example, a mixture of t-butyl alcohol and water, or an acetic acid buffer) in the presence of 2 to 10 equivalents of a chlorine scavenger (for example, sulfamic acid or resorcinol) at room temperature for 30 min to 6 hr, preferably 30 min to 2 hr. The esterification is carried out by reacting the compound thus obtained with 1.5 to 10 equivalents of a diazo $C_1$–$C_5$ alkane in a solvent (for example, hexane or methanol) at room temperature for 30 min to 5 hr.

Therefore, in the step (ii), the compound represented by the formula (IIIb) is reduced to give a compound corresponding to the formula (II). This reaction may be carried out by reducing the epoxy with 3 to 10 equivalents of iodine and 3 to 10 equivalents of triphenylphosphine in a solvent (for example, an aromatic hydrocarbon, such as benzene, toluene, or xylene, an ether, such as tetrahydrofuran, dioxane, 1,2-dimethoxyethane, diethyl ether, or diisopropyl ether, or a halogenated hydrocarbon, such as dichloromethane, chloroform, carbon tetrachloride, or 1,2-dichloroethane) at room temperature for 1 to 24 hr, preferably 1 to 6 hr.

In the step (iii), a reduction reaction is carried out to give a compound corresponding to the formula (I). In this reaction, 4 to 20 equivalents of a reducing agent selected from sodium boron hydride, calcium boron hydride, lithiumtributoxyaluminum hydride, diborane, sodium boron hydride cyanide and the like is used to conduct cyclization under ice cooling or at room temperature for 30 min to 24 hr.

Alternatively, the compound corresponding to the formula (II) prepared in the step (ii) may be subjected to the step (iv) to give another compound corresponding to the formula (I). This reaction is carried out using 1.5 to 10 equivalents of a reducing agent selected from sodium boron hydride, calcium boron hydride, lithiumtributoxyaluminum hydride, diborane, sodium boron hydride cyanide and the like in a solvent (for example, an alcohol, such as methanol, ethanol, or propanol, or an ether, such as tetrahydrofuran, dioxane, dimethoxyethane, diethyl ether, or diisopropyl ether), optionally in the presence of cerium(III) chloride heptahydrate as a catalyst, at room temperature for 1 to 24 hr, preferably 1 to 6 hr. Further, the compounds represented by the formula (I) may be prepared by a process according to the following scheme 2.

Scheme 2

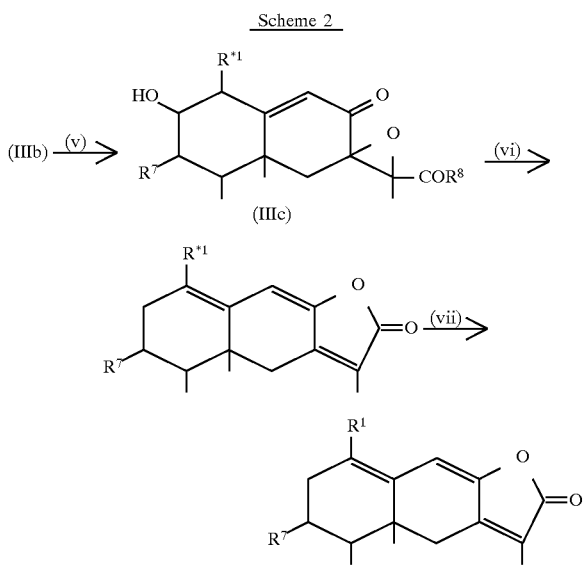

The compound represented by the formula (IIIb) prepared above may be subjected to the step (v) to give a compound represented by the formula (IIIc) wherein $R^{*1}$ represents a halogen atom. This halogenation may be carried out using 10 to 50 equivalents of a halide at room temperature for 20 min to 24 hr, preferably 20 min to 6 hr. Preferred examples of halides include, for example, hydrogen halides (for example, hydrogen bromide and hydrochloric acid), phosphorus halides (for example, phosphorus pentachloride, phosphorus acid chloride, and phosphorus tribromide), thionyl halides (for example, thionyl chloride and thionyl bromide), and phosphine and halides (for example, triphenyl phosphine and carbon tetrabromide or carbon tetrachloride). The solvent used is not particularly limited so far as the reaction proceeds. However, preferred are, for example, alcohols, such as methanol, ethanol and propanol, aromatic hydrocarbons, such as benzene, toluene, and xylene, ethers, such as tetrahydrofuran, dioxane, 1,2-dimethoxyethane, diethyl ether, and diisopropyl ether, and halogenated hydrocarbons, such as dichloromethane, chloroform, carbon tetrachloride, and 1,2-dichloroethane.

The compound represented by the formula (IIIc) is then subjected to the step (vi) to give a compound corresponding to the formula (I). This dehydration reaction may be carried out using 1.2 to 5 equivalents of a dehydrating agent, such as thionyl chloride, phosphorus pentaoxide, phosphorus pentachloride, or benzoyl chloride, in a solvent (for example, pyridine or chloroform) in the presence of a basic catalyst, such as pyridine, triethylamine, or dimethylaminopyridine, at room temperature for 1 to 24 hr, preferably 1 to 6 hr.

The compound thus obtained may be subjected to reduction cyclization in the step (vii) and further converted to a phenylthio or alkoxy form to give a compound corresponding to the formula (I). The reduction cyclization is carried out using 3 to 10 equivalents of iodine and a 3 to 10 equivalents of a reducing agent, such as triphenylphosphine, either at room temperature for 1 to 24 hr or at 90° to 120° C. for 10 to 30 min to convert one or two epoxys to iodohydrin, followed by dehydration or further reduction cyclization. Further, a reaction at 90° to 120° C. for 1 to 6 hr, preferably 1 to 3 hr, permits one epoxy to be reduced with decarboxylation. The conversion to a phenylthio or alkoxy form may be carried out by reacting the compound with 1 to 2 equivalents of thiophenol or a $C_1$–$C_5$ alkyl alcohol in excess in a solvent (for example, water or ethanol) in the presence of a base, such as 1.2 to 2 equivalents of sodium carbonate or potassium carbonate at 25° to 120° C. for 1 to 5 hr.

According to another embodiment of the present invention, the compounds represented by the formula (III) are provided as preferred intermediate for the synthesis of the compounds represented by the formula (I) or (II).

In the formula (III), $R^5$ and $R^7$ are as defined for $R^1$ in formula (I) above, and preferred examples thereof include those described in connection with $R^1$.

Some of the compounds represented by the formula (III) are embraced in the formula (II), indicating that some of the compounds represented by the formula (II) may be used as intermediates for the synthesis of the compounds represented by the formula (I).

Specific examples of the compounds represented by the formula (III) include:

3β-acetoxy-1β(2β),7β(11β)-diepoxy-8-oxoeremophil-9 (10)-en-12-oic acid;

3β-acetoxy-1β(2β),7β(11β)-diepoxy-8-oxoeremophil-9 (10)-en-12-oic acid methyl ester;

3β-acetoxy-1α-chloro-7β(11β)-epoxy-2β-hydroxy-8-oxoeremophil-9(10)-en-12-oic acid methyl ester; and 3β-acetoxy-8-oxoeremophila-1(2),7(11),9(10)-trien-12-oic acid methyl ester.

EXAMPLES

The present invention will be described in more detail with reference to the following examples, though it is not limited to these examples only.

EXAMPLE 1

3β-Acetoxy-1β(2β),7β(11β)-diepoxy-8-oxoeremophil-9 (10)-en-12-oic acid

A solution of sodium chlorite (576.5 ml, 6.37 mM) in water (10 ml) and a solution of sulfamic acid (618.6 mg, 6.37 mM) in water (10 ml) were added to a t-butanol (100 ml) solution containing PR toxin (1.7 g, 5.31 mM), and the mixture was stirred at room temperature for one hr. Water was added to the reaction solution, followed by extraction with ethyl acetate. The organic layer was washed with saturated saline and water. It was then dried over anhydrous sodium sulfate, and the solvent was removed by distillation under reduced pressure. The residue was purified by chromatography on silica gel (eluting solvent: chloroform/methanol=2/1) to give the title compound (1.48 g, yield 83%).

$^1$H-NMR (CD$_3$OD): δ1.10 (d, J=7.2 Hz, 3H), 1.42 (s, 3H), 1.64 (s, 3H), 1.97 (d, J=14.4 Hz, 1H), 1.98 (m, 1H), 2.18 (s, 3H), 2.35 (d, J=14.6 Hz, 1H), 3.81 (d, J=3.6 Hz, 1H), 4.00

(dd, J=3.6, 4.9 Hz, 1H), 5.20 (dd, J=4.9, 5.1, 1H), 6.51 (s, 1H) MS (SI): m/z=337 (MH$^+$)

EXAMPLE 2

3β-Acetoxy-1β(2β),7β(11β)-diepoxy-8-oxoeremophil-9(10)-en-12-oic acid methyl ester A reagent composed of a 10% solution of trimethylsilyldiazomethane in n-hexane was gradually dropwise added at room temperature to a methanol solution (5 ml) containing the compound (100 mg, 0.298 mM) prepared in Example 1 until the reaction solution assumed a yellow color. Further, one drop of acetic acid was added thereto, and the solvent was then removed by distillation under reduced pressure. The residue was washed with n-hexane to give the title compound (95 mg, yield 91%).

$^1$H-NMR (CDCl$_3$): δ1.01 (d, J=6.9 Hz, 3H), 1.39 (s, 3H), 1.59 (s, 3H), 2.15 (s, 3H), 3.63 (d, J=3.8 Hz, 1H), 3.85 (s, 3H), 3.93 (dd, J=3.8, 4.9 Hz, 1H), 5.13 (dd, J=3.9, 4.9 Hz, 1H), 6.39 (s, 1H) MS (EI): m/z=350 (M$^+$)

EXAMPLE 3a

3β-Acetoxy-1β(2β),7β(11β)-diepoxy-8-hydroxyeremophil-9(10)-en-12-oic acid methyl ester Cerium(III) chloride heptahydrate (74.5 mg, 0.2 mM) and sodium boron hydride in excess were added to a methanol solution (5 ml) containing the compound (67 mg, 0.2 mM) prepared in Example 2, and the mixture was stirred at room temperature for 30 min. Water was added to the reaction solution, followed by extraction with dichloromethane. The solvent was removed by distillation, and the residue was purified by chromatography on silica gel (eluting solvent: chloroform/ethyl acetate=1/1) to give the title compound (21.2 mg, yield 31.5%).

$^1$H-NMR (CDCl$_3$): δ0.95 (s, 3H), 1.22 (s, 3H), 1.44 (d, J=13.7 Hz, 1H), 1.61 (s, 3H), 1.68 (m, 1H), 1.89 (d, J=13.0 Hz, 1H), 2.13 (s, 3H), 3.56 (d, J=3.8 Hz, 1H), 3.74 (dd, J=3.8, 5.4 Hz, 1H), 3.81 (dd, J=1.1, 4.6 Hz, 1H), 5.10 (dd, J=5.3, 5.3 Hz, 1H), 6.05 (d, J=5.0 Hz, 1H) MS (SI): m/z=353 (MH$^+$)

EXAMPLE 3b

3β-Acetoxy-1β(2β),7β(11β)-diepoxyeremophil-9(10)-en-12,8β-olide

In Example 3a, the title compound (5.2 mg, yield 8.5%), together with the compound described in Example 3a, was obtained.

$^1$H-NMR (CDCl$_3$): δ1.01 (d, J=7.0 Hz, 3H), 1.28 (s, 3H), 1.50 (s, 3H), 1.73 (m, 1H), 1.83 (d, J=15.6 Hz, 1H), 1.99 (d, J=15.2 Hz, 1H), 2.14 (s, 3H), 3.58 (d, J=1.5 Hz, 1H), 3.75 (dd, J=3.5, 5.1 Hz, 1H), 5.00 (d, J=1.6 Hz, 1H), 5.14 (dd, J=5.1, 5.5 Hz, 1H), 6.09 (d, J=1.5 Hz, 1H) MS (SI): m/z=321 (MH$^+$)

EXAMPLE 4

3β-Acetoxy-7β(11β)-epoxyeremophila-1(2),9(10)-dien-12,8β-olide

The compound (2.0 mg, 6.25 μM) prepared in Example 3b was dissolved in dichloromethane (0.5 ml). Triphenylphosphine (1.6 mg, 7.63 μM) and iodine (4.0 mg, 15.8 μM) were added to the solution, and the mixture was stirred at room temperature for one hr. A 5% aqueous sodium thiosulfate solution (3 ml) was added to the reaction solution, followed by extraction with chloroform. The organic layer was washed with water and then dried over anhydrous sodium sulfate, and the solvent was removed by distillation under reduced pressure. The residue was purified by preparative TLC (developing solvent: chloroform/ethyl acetate=3/1) to give the title compound (0.7 mg, yield 37%).

$^1$H-NMR (CDCl$_3$): δ1.07 (d, J=7.2 Hz, 3H), 1.24 (s, 3H), 1.50 (s, 3H), 1.84 (d, J=15.2 Hz, 1H), 1.94 (m, 1H), 2.07 (s, 3H), 2.08 (d, J=15.2 Hz, 1H), 5.07 (brs, 1H), 5.24 (dd, J=5.3, 5.3 Hz, 1H), 5.74 (d, J=1.9 Hz, 1H), 6.02 (dd, J=5.7, 9.5 Hz, 1H), 6.22 (d, J=9.9 Hz, 1H)

EXAMPLE 5

3β-Acetoxy-1α-chloro-7β(11β)-epoxy-2β-hydroxy-8-oxoeremophil-9(10)-en-12-oic acid methyl ester A reagent (80 ml) composed of a 10% solution of hydrochloric acid in methanol was added under ice cooling to the compound (1.0 g, 2.97 mM) prepared in Example 1, and the mixture was stirred at room temperature for 2 hr. Water was added to the reaction solution under ice cooling, followed by extraction with ethyl acetate. The organic layer was washed with water and dried over anhydrous sodium sulfate, and the solvent was removed by distillation under reduced pressure. The residue was purified by chromatography on silica gel (eluting solvent: chloroform/methanol=10/1) to give the title compound (882 mg, yield 77%).

$^1$H-NMR (CDCl$_3$): δ1.08 (d, J=7.2 Hz, 3H), 1.44 (s, 3H), 1.67 (s, 3H), 1.86 (m, 1H), 2.05 (d, J=14.6 Hz, 1H), 2.16 (d, J=14.6 Hz, 1H), 2.19 (s, 3H), 3.79 (m, 1H), 3.84 (s, 3H), 4.97 (dd, J=2.1, 11.0 Hz, 1H), 5.52 (dd, J=3.1, 3.3 Hz, 1H), 6.68 (d, J=2.1 Hz, 1H) MS (FD): m/z=386 (M$^+$)

EXAMPLE 6

3β-Acetoxy-1-chloro-11β-hydroxy-8-oxoeremophila-1(2),6(7),9(10)-trien-12-oic acid methyl ester The compound (4.2 mg, 0.01 mM) prepared in Example 1 was dissolved under ice cooling in a reagent (1 ml) composed of a 10% solution of hydrochloric acid in methanol, the temperature of the solution was raised to 25° C., and the solution was then stirred at that temperature for 4.5 hr. Methanol contained in the reaction solution was removed by distillation under reduced pressure, and water was added to the residue, followed by extraction with chloroform. The solvent was removed by distillation under reduced pressure, and the residue was purified by preparative TLC (developing solvent: chloroform/methanol=10/1) to give the title compound (1.6 mg, yield 35%) and the compound (1.8 mg, yield 37%) described in Example 5.

$^1$H-NMR (CDCl$_3$): δ1.24 (d, J=7.2 Hz, 3H), 1.42 (s, 1H), 1.62 (s, 3H), 2.15 (s, 3H), 2.23 (m, 1H), 3.74 (s, 3H), 5.50 (dd, J=5.1, 5.4 Hz, 1H), 6.37 (d, J=5.6 Hz, 1H), 6.66 (s, 1H), 7.10 (s, 1H) MS (FD): m/z=368 (M$^+$)

EXAMPLE 7a

3β-Acetoxy-1-chloroeremophila-1(10),7(11),8(9)-trien-12,8-olide

The compound (20 mg, 0.05 mM) prepared in Example 5 was dissolved in 1,2-dichloroethane (1.5 ml). Iodine (64 mg, 0.25 mM) and triphenylphosphine (65 mg, 0.25 mM) were added to the solution, and the mixture was stirred at 95° C. for 10 min. A 5% aqueous sodium thiosulfate solution (25 ml) was added to the reaction solution, followed by extraction with chloroform. The solvent was removed by distillation under reduced pressure. The residue was purified by preparative TLC (developing solvent: hexane/ethyl acetate=2/1) to give the title compound (2.2 mg, yield 13%).

$^1$H-NMR (CDCl$_3$): δ1.12 (d, J=7.2 Hz, 3H), 1.18 (s, 3H), 1.95 (d, J=1.8 Hz, 3H), 1.95 (m, 1H), 2.10 (s, 3H), 2.27 (d, J=15.1 Hz, 1H), 2.65 (d, J=19.5 Hz, 1H), 2.86 (d, J=16.4 Hz, 1H), 2.95 (dd, J=5.9, 20.3 Hz, 1H), 5.16 (m, 1H), 6.51 (s, 1H) MS (FAB): m/z=323 (MH$^+$)

EXAMPLE 7b

3β-Acetoxyeremophila-1(10),7(11),8(9)-trien-12,8-olide

In Example 7a, the title compound (1.4 mg, yield 9.5%), together with the compound described in Example 7a, was obtained.

$^1$H-NMR (CDCl$_3$): δ1.11 (d, J=7.2 Hz, 3H), 1.17 (s, 3H), 1.93 (d, J=1.8 Hz, 3H), 1.93 (m, 1H), 2.07 (s, 3H), 2.22 (br-d, J=17.7 Hz, 1H), 2.42 (dd, J=5.0, 20.3 Hz, 1H), 2.61 (m, 1H), 2.86 (d, J=15.6 Hz, 1H), 5.16 (m, 1H), 5.73 (m, 1H), 5.99 (s, 1H) MS (SI): m/z=289 (MH$^+$)

EXAMPLE 7c

3β-Acetoxy-1-chloro-11β-hydroxy-8-oxoeremophila-1(2),9(10)-dien-12-oic acid methyl ester In Example 7a, the title compound (3.1 mg, yield 16%), together with the compounds described in Examples 7a and 7b, was obtained.

$^1$H-NMR (CDCl$_3$): δ1.06 (d, J=6.9 Hz, 3H), 1.31 (s, 3H), 1.50 (s, 3H), 2.02–2.11 (m, 3H), 2.12 (s, 3H), 2.82 (dd, J=6.2, 12.6 Hz, 1H), 3.75 (s, 3H), 5.40 (dd, J=5.1, 5.4 Hz, 1H), 6.40 (s, 1H), 6.49 (d, J=5.6 Hz, 1H) MS (FAB): m/z=371 (MH$^+$)

EXAMPLE 8

3β-Acetoxy-1-chloro-11β-hydroxyeremophila-1(2),9(10)-dien-12,8β-olide

The compound (22.5 mg, 0.06 mM) prepared in Example 7c was dissolved in methanol (8 ml). Sodium boron hydride (2.0 mg, 0.05 mM) and a catalytic amount of cerium(III) chloride heptahydrate were added to the solution, and the mixture was stirred at room temperature for one hr. Water was added to the reaction solution, and the solution was made acidic by the addition of 6 N hydrochloric acid, followed by extraction with ethyl acetate. The organic layer was dried over anhydrous sodium sulfate, and the solvent was removed by distillation under reduced pressure. The residue was purified by preparative TLC (developing solvent: chloroform/ethyl acetate=5/2) to give the title compound (9.9 mg, yield 48.1%).

$^1$H-NMR (CDCl$_3$): δ1.01 (d, J=7.2 Hz, 3H), 1.16 (s, 3H), 1.45 (s, 3H), 1.71 (m, 1H), 1.87 (m, 1H), 2.08 (s, 3H), 2.35 (brs, 1H), 2.56(ddd, J=4.9, 4.9, 14.3 Hz), 5.23 (dd, J=4.9, 5.1 Hz, 1H), 5.33 (dd, J=4.9, 5.1 Hz, 1H), 6.23 (d, J=5.6 Hz, 1H), 6.41 (d, J=4.6, 1H) MS (EI): m/z=340 (M$^+$)

EXAMPLE 9

3β-Acetoxy-1-chloroeremophila-1(2),9(10),11(13)-trien-12,8β-olide

The compound (5.2 mg, 0.0153 mM) prepared in Example 8 was dissolved in pyridine (1 ml). A catalytic amount of thionyl chloride was added to the solution, and the mixture was stirred at room temperature for 3 hr. Water was added to the reaction solution, followed by extraction with ethyl acetate. The organic layer was dried over anhydrous sodium sulfate, and the solvent was removed by distillation under reduced pressure. The residue was purified by preparative TLC (developing solvent: chloroform/ethyl acetate=5/2) to give the title compound (3.5 mg, yield 71.1%).

$^1$H-NMR (CDCl$_3$): δ1.02 (d, J=7.2 Hz, 3H), 1.19 (s, 3H), 1.85–1.96 (m, 3H), 2.09 (s, 3H), 4.96 (dd, J=4.1, 6.7 Hz, 1H), 5.31 (dd, J=5.4, 5.4 Hz, 1H), 5.70 (d, J=1.5 Hz, 1H), 6.25 (d, J=5.6 Hz, 1H), 6.28 (d, J=1.8 Hz, 1H), 6.43 (d, J=4.3 Hz, 1H) MS (EI): m/z=322 (M$^+$)

EXAMPLE 10

3β-Acetoxy-1-chloro-8,11β-dihydroxyeremophila-1(2),6(7),9(10)-trien-12-oic acid methyl ester The compound (5 mg, 0.014 mM) prepared in Example 6 was dissolved in methanol (0.5 ml). A solution of 0.01 mM cerium(III) heptahydrate in methanol (140 μl, 0.014 mM) and a 1.0 mM solution of sodium boron hydride in methanol (7 μl, 0.007 mM) were added to the solution, and the mixture was stirred at 25° C. for 2 hr. Methanol contained in the reaction solution was removed by distillation under reduced pressure, and water was added thereto, followed by extraction with chloroform. The solvent was removed by distillation under reduced pressure, and the residue was purified by preparative TLC (developing solvent: chloroform/ethyl acetate=3/1) to give the title compound (0.7 mg, yield 14%).

$^1$H-NMR (CDCl$_3$): δ1.13 (d, J=7.3 Hz, 3H), 1.14 (s, 3H), 1.63 (s, 3H), 2.09 (s, 3H), 2.09 (m, 1H), 3.75 (s, 3H), 5.34 (dd, J=4.8, 4.8 Hz, 1H), 6.04 (d, J=1.2 Hz, 1H), 6.09 (d, J=5.6 Hz, 1H), 6.35 (d, J=2.7 Hz, 1H) MS (EI): m/z=370 (M$^+$)

EXAMPLE 11

3β-Acetoxy-1-chloro-5-demethyl-5,6,7,8,9,10-hexadehydro-11β-hydroxy-6-methyleremophil-1(2)-en-12-oic acid methyl ester The compound (9.5 mg, 0.026 mM) prepared in Example 10 was dissolved in toluene (1 ml). p-Toluenesulfonic acid (1 mg, 0.005 mM) was added to the solution, and the mixture was stirred at 25° C. for 1.5 hr. Toluene contained in the reaction solution was removed by distillation under reduced pressure, and water was added to the residue, followed by extraction with chloroform. The solvent was removed by distillation under reduced pressure, and the residue was purified by preparative TLC (developing solvent: chloroform/ethyl acetate=3/1) to give the title compound (3.6 mg, yield 40%).

$^1$H-NMR (CDCl$_3$): δ1.11 (d, J=6.9 Hz, 3H), 1.85 (s, 3H), 2.16 (s, 3H), 2.24 (s, 3H), 3.46 (m, 1H), 3.78 (s, 3H), 5.75 (dd, J=1.9, 6.7 Hz, 1H), 5.93 (dd, J=1.7, 1.7 Hz, 1H), 7.43 (d, J=8.3 Hz, 1H), 7.51 (d, J=8.6 Hz, 1H) MS (EI): m/z=352 (M$^+$)

EXAMPLE 12

3β-Acetoxy-1α-chloro-2β,11β-dihydroxy-8-oxoeremophil-9(10)-en-12-oic acid methyl ester The compound (20 mg, 0.05 mM) prepared in Example 5 was dissolved in methylene chloride (2 ml). Iodine (40 mg, 0.15 mM) and triphenylphosphine (41 mg, 0.15 mM) were added to the solution, and the mixture was stirred at 25° C. for 18 hr. A 5% aqueous sodium thiosulfate solution (25 ml) was added to the reaction solution, followed by extraction with chloroform. The solvent was removed by distillation under reduced pressure. The residue was purified by preparative TLC (developing solvent: chloroform/methanol=20/1) to give the title compound (5.6 mg, yield 27%).

$^1$H-NMR (CDCl$_3$): δ1.06 (d, J=7.2 Hz, 3H), 1.37 (s, 3H), 1.49 (s, 3H), 1.78 (m, 1H), 2.08 (m, 1H), 2.19 (s, 3H), 2.78 (dd, J=5.6, 13.6 Hz, 1H), 3.76 (s, 3H), 4.87 (dd, J=1.9, 10.8 Hz, 1H), 5.49 (dd, J=3.1, 3.3 Hz, 1H), 6.47 (d, J=1.9 Hz, 1H) MS (CI): m/z=389 (MH$^+$)

EXAMPLE 13

3β-Acetoxy-1-chloro-8-oxoeremophila-1(2),7(11),9(10)-trien-12-oic acid methyl ester The compound (2.7 mg, 0.007 mM) prepared in Example 12 was dissolved in pyridine (1 ml). Thionyl chloride (one drop) was added to the solution, and the mixture was stirred at 25° C. for one hr. The solvent contained in the reaction solution was removed by distillation under reduced pressure, and water was added to the residue, followed by extraction with chloroform. The solvent was removed by distillation under reduced pressure, and the residue was purified by preparative TLC (developing solvent: chloroform/ethyl acetate=3/1) to give the title compound (0.2 mg, yield 8.2%).

$^1$H-NMR (CDCl$_3$): δ1.11 (d, J=6.9 Hz, 3H), 1.22 (s, 3H), 2.04 (d, J=1.9 Hz, 3H), 2.11 (s, 3H), 2.11 (m, 1H), 2.30 (m, 1H), 2.90 (d, J=14.2 Hz, 1H), 3.83 (s, 3H), 5.42 (dd, J=4.4, 5.8 Hz, 1H), 6.50 (d, J=5.3 Hz, 1H), 6.50 (s, 1H) MS (FAB): m/z=353 (MH$^+$)

EXAMPLE 14a

3β-Acetoxy-8-oxoeremophila-1(2),7(11),9(10)-trien-12-oic acid methyl ester

The compound (20 mg, 0.06 mM) prepared in Example 2 was dissolved in methylene chloride (2 ml). Iodine (74 mg, 0.29 mM) and triphenylphosphine (71 mg, 0.27 mM) were added to the solution, and the mixture was stirred at 25° C. for 2.5 hr. A 5% aqueous sodium thiosulfate solution (25 ml) was added to the reaction solution, followed by extraction with chloroform. The solvent was removed by distillation under reduced pressure. The residue was purified by preparative TLC (developing solvent: chloroform/ethyl acetate=3/1) to give the title compound (1.0 mg, yield 5.4%).

$^1$H-NMR (CDCl$_3$): δ1.11 (d, J=7.2 Hz, 3H), 1.20 (s, 3H), 2.04 (d, J=2.1 Hz, 3H), 2.04 (m, 1H), 2.10 (s, 3H), 2.26 (m, 1H), 2.89 (d, J=14.1 Hz, 1H), 3.82 (s, 3H), 5.38 (dd, J=4.9, 5.1 Hz, 1H), 5.89 (s, 1H), 6.27 (dd, J=4.9, 9.6 Hz, 1H), 6.36 (d, J=9.8 Hz, 1H) MS (EI): m/z=318 (M$^+$)

EXAMPLE 14b

3β-Acetoxy-11β-hydroxy-8-oxoeremophila-1(2),9(10)-dien-12-oic acid methyl ester

In Example 14a, the title compound (1.2 mg, yield 6.2%), together with the compound described in Example 14a, was obtained.

$^1$H-NMR (CDCl$_3$): δ1.06 (d, J=7.2 Hz, 3H), 1.28 (s, 3H), 1.49 (s, 3H), 1.98 (m, 1H), 2.03 (m, 1H), 2.10 (m, 1H), 2.11 (s, 3H), 2.80 (ss, J=4.9, 13.3 Hz, 1H), 3.74 (s, 3H), 5.37 (dd, J=4.9, 5.1 Hz, 1H), 5.80 (s, 1H), 6.27 (dd, J=5.1, 10.0 Hz, 1H), 6.34 (d, J=9.7 Hz, 1H) MS (FAB): m/z=337 (MH$^+$)

EXAMPLE 15

3β-Acetoxyeremophila-1(2),7(11),9(10)-trien-12,8β-olide

The compound (18 mg, 0.0566 mM) prepared in Example 14a was dissolved in methanol (1 ml). Sodium boron hydride was added in excess to the solution, and the mixture was stirred under ice cooling for 30 min. Water was added to the reaction solution, followed by extraction with ethyl acetate. The organic layer was dried over anhydrous sodium sulfate, and the solvent was removed by distillation under reduced pressure. The residue was purified by preparative TLC (developing solvent: n-hexane/ethyl acetate=2/1) to give the title compound (2.8 mg, yield 17%).

$^1$H-NMR (CDCl$_3$): δ0.98 (s, 3H), 1.07 (d, J=7.2 Hz, 3H), 1.88 (s, 3H), 2.06 (s, 3H), 2.06 (m, 1H), 2.26 (d, J=12.2 Hz), 2.83 (d, J=12.6 Hz), 5.27 (brs, 1H), 5.32 (dd, J=4.5, 4.9 Hz, 1H), 5.74 (d, J=2.6 Hz, 1H), 5.89 (dd, J=4.9, 9.5 Hz, 1H), 6.15 (d, J=9.2 Hz, 1H) MS (EI): m/z=288 (M$^+$)

EXAMPLE 16

Eremophila-1(10),2(3),7(11),8(9)-tetraen-12,8-olide

The compound (63 mg, 0.2 mM) prepared in Example 14a was dissolved in methanol (2 ml). Sodium boron hydride (5 mg, 0.132 mM) and a catalytic amount of cerium chloride were added to the solution, and the mixture was stirred at room temperature for 16 hr. Water was added to the reaction solution, followed by extraction with ethyl acetate. The organic layer was dried over anhydrous sodium sulfate, and the solvent was removed by distillation under reduced pressure. The residue was purified by preparative TLC (developing solvent: n-hexane/ethyl acetate=5/1) to give the title compound (8 mg, yield 12.7%) and the compound described in Example 7b (2 mg, yield 3%).

$^1$H-NMR (CDCl$_3$): δ0.70 (s, 3H), 1.15 (d, J=7.2 Hz, 3H), 1.94 (s, 3H), 2.21 (d, J=16.8 Hz, 1H), 2.40 (m, 1H), 2.88 (d, J=16.8 Hz, 1H), 5.68 (m, 1H), 6.11 (m, 3H) MS (EI): m/z=228 (M$^+$)

EXAMPLE 17

3β-Acetoxy-11-demethyl-1β(2β)-epoxy-8-oxoeremophila-7(11),9(10)-dien-11-ol

The compound prepared in Example 1 (50 mg, 0.149 mM), triphenylphosphine (10 mg, 0.038 mM), and sodium iodide (10 mg, 0.067 mM) were suspended in toluene (10 ml), and the suspension was heated under reflux for 1.5 hr. Water was added thereto, followed by extraction with toluene. The organic layer was dried over anhydrous sodium sulfate, and the solvent was removed by distillation under reduced pressure. The residue was purified by preparative TLC (developing solvent: chloroform/ethyl acetate=3/1) to give the title compound (8.9 mg, yield 20.5%).

$^1$H-NMR (CDCl$_3$): δ1.01 (d, J=7.2 Hz, 3H), 1.11 (s, 3H), 1.76 (m, 1H), 2.12 (s, 3H), 2.14 (s, 3H), 2.22 (d, J=14.4 Hz, 1H), 2.42 (d, J=14.4 Hz, 1H), 3.59 (d, J=3.3 Hz, 1H), 3.87 (dd, J=3.6, 5.0 Hz, 1H), 5.11 (dd, J=5.0, 5.0 Hz, 1H), 6.29 (s, 1H) MS (EI): m/z=292 (M$^+$)

EXAMPLE 18a

3β-Acetoxy-1α,7α-dichloro-2β,11β-dihydroxy-8,12-dioxoeremophil-9(10)-ene

PR toxin (100 mg, 0.31 mM) was dissolved in a reagent (5 ml) composed of a 10% solution of hydrochloric acid in methanol, and the solution was then stirred at 25° C. for 20 min. Methanol contained in the reaction solution was removed by distillation under reduced pressure, and water was added to the residue, followed by extraction with chloroform. The solvent was removed by distillation under reduced pressure, and the residue was purified by preparative TLC (developing solvent: chloroform/ethyl acetate=2/1) to give the title compound (19.4 mg, yield 16%).

$^1$H-NMR (CDCl$_3$): δ1.13 (d, J=7.0 Hz, 3H), 1.40 (s, 6H), 2.20 (s, 3H), 2.51 (d, J=16.4 Hz, 1H), 2.65 (d, J=16.4 Hz, 1H), 2.80 (m, 1H), 3.66 (dd, J=3.9, 10.6 Hz, 1H), 5.01 (dd, J=1.6, 10.6 Hz, 1H), 5.54 (dd, J=3.9, 3.9 Hz, 1H), 6.59 (d, J=1.2 Hz, 1H), 10.08 (s, 1H) MS (FAB): m/z=393 (MH$^+$)

EXAMPLE 18b

3β-Acetoxy-7α-chloro-2β,11β-dihydroxy-8,12-dioxo-1α-methoxyeremophil-9(10)-ene

In Example 18a, the title compound (10.4 mg, yield 8.6%), together with the compound described in Example 18a, was obtained.

$^1$H-NMR (CDCl$_3$): δ1.10 (d, J=7.0 Hz, 3H), 1.37 (s, 3H), 1.40 (s, 3H), 2.19 (s, 3H), 2.49 (d, J=16.0 Hz, 1H), 2.61 (d, J=16.4 Hz, 1H), 2.76 (m, 1H), 3.49 (s, 3H), 3.58 (dd, J=3.9, 9.8 Hz, 1H), 4.17 (dd, J=1.6, 9.8 Hz, 1H), 5.49 (dd, J=3.9, 3.9 Hz, 1H), 6.22 (d, J=1.2 Hz, 1H), 10.09 (s, 1H) MS (FAB): m/z=389 (MH$^+$)

EXAMPLE 19a

1-Chloro-3β, 11β-dihydroxy-8-oxoeremophila-1(2),6(7),9(10)-trien-12-oic acid methyl ester The compound (300 mg, 0.91 mM) prepared in Example 1 was dissolved in a reagent (20 ml) composed of a 10% solution of hydrochloric acid in methanol, and the solution was then stirred at 25° C. for 24.5 hr. Methanol contained in the reaction solution was removed by distillation under reduced pressure, and water was added to the residue, followed by extraction with chloroform. The solvent was removed by distillation under reduced pressure, and the residue was purified by chromatography on silica gel (eluting solvent: chloroform/ethyl acetate=10/1) and preparative TLC (developing solvent: chloroform/ethyl acetate=3/1) to give the title compound (111 mg, yield 38%).

$^1$H-NMR (CDCl$_3$): δ1.34 (d, J=7.3 Hz, 3H), 1.44 (s, 3H), 1.63 (s, 3H), 2.04 (m, 1H), 3.74 (s, 3H), 4.38 (br-dd, J=5.0, 5.0 Hz, 1H), 6.42 (d, J=4.9 Hz, 1H, 6.62 (s, 1H), 7.12 (s, 1H) MS (SI): m/z 327 (MH$^+$)

EXAMPLE 19b

1-Chloro-11β-hydroxy-3β-methoxy-8-oxoeremophila-1(2), 6(7),9(10)-trien-12-oic acid methyl ester In Example 19a, the title compound (6.1 mg, yield 2.0%), together with the compound described in Example 19a, was obtained.

$^1$H-NMR (CDCl$_3$): δ1.18 (s, 3H), 1.30 (d, J=6.7 Hz, 3H), 1.63 (s, 3H), 1.85 (m, 1H), 3.45 (s, 3H), 3.70 (dd, J=2.6, 9.5 Hz, 1H), 3.74 (s, 3H), 6.48 (d, J=2.6 Hz, 1H), 6.66 (s, 1H), 7.13 (s, 1H) MS (FD): m/z=340 (M$^+$)

EXAMPLE 20

3β-Acetoxy-1-chloro-8-oxoeremophila-1(2),9(10),11(13)-trien-12-oic acid methyl ester The compound (14 mg, 0.04 mM) prepared in Example 7c was dissolved in pyridine (1 ml). Thionyl chloride (one drop) was added to the solution, and the mixture was stirred at 25° C. for 3 hr. Water was added to the reaction solution, followed by extraction with chloroform. The solvent was removed by distillation under reduced pressure, and the residue was purified by preparative TLC (developing solvent: chloroform/ethyl acetate=5/1) to give the title compound (1.3 mg, yield 9.8%) and the compound (1.3 mg, yield 9.8%) described in Example 13.

$^1$H-NMR (CDCl$_3$): δ1.04 (d, J=7.2 Hz, 3H), 1.37 (s, 3H), 2.03 (m, 1H), 2.09 (m, 1H), 2.12 (s, 3H), 3.64 (dd, J=5.4, 13.4 Hz, 1H), 3.77 (s, 3H), 5.41 (dd, J=5.1, 5.4 Hz, 1H), 5.72 (s, 1H), 6.40 (d, J=0.8 Hz, 1H), 6.46 (d, J=5.6 Hz, 1H), 6.47 (s, 1H) MS (FAB): m/z=353 (MH$^+$)

EXAMPLE 21a

3β-Acetoxy-1-phenylthioeremophila-1(10),7(11),8(9)-trien-12,8-olide

A solution of the compound (10.3 mg, 0.032 mM), prepared in Example 7a, in ethanol (0.5 ml) was added to a solution of thiophenol (3.1 μl, 0.03 mM) and sodium carbonate (3.7 mg, 0.035 mM) in water (0.5 ml), and the mixture was stirred at 110° C. for 2 hr. Water was added to the reaction solution, followed by extraction with chloroform. The residue was purified by preparative TLC (developing solvent: hexane/acetone=2/1) to give the title compound (0.5 mg, yield 3.9%).

$^1$H-NMR (CDCl$_3$): δ1.11 (d, J=7.2 Hz, 3H), 1.15 (s, 3H), 1.91 (m, 1H), 1.95 (d, J=1.8 Hz, 3H), 1.97 (s, 3H), 2.27 (br-d, J=16.7 Hz, 1H), 2.32 (m, 1H), 2.50 (m, 1H), 2.89 (d, J=16.2 Hz, 1H), 5.05 (m, 1H), 6.36 (m, 1H), 7.15–7.30 (m, 5H) MS (EI) m/z=396 (M$^+$)

EXAMPLE 21b

3β-Acetoxy-1-ethoxyeremophila-1(10),7(11),8(9)-trien-12,8-olide

In Example 21a, the title compound (0.4 mg, yield 3.8%), together with the compound described in Example 21a, was obtained.

$^1$H-NMR (CDCl$_3$): δ1.11 (d, J=6.7 Hz, 3H), 1.15 (s, 3H), 1.38 (t, J=7.1 Hz, 3H), 1.91 (d, J=1.7 Hz, 3H), 1.93 (m, 1H), 2.05 (s, 3H), 2.18 (br-d, J=15.0 Hz, 1H), 2.46 (m, 1H), 2.60 (m, 1H), 2.82 (d, J=16.0 Hz, 1H), 4.37 (dq, J=6.7, 9.3 Hz, 1H), 4.63 (dq, J=6.7, 9.3 Hz, 1H) 5.12 (m, 1H), 6.32 (m, 1H) MS (FAB) m/z=333 (MH$^+$)

TEST EXAMPLE

Activity Evaluation Test

The progesterone receptor binding inhibitory activity of the compounds of the present invention was measured in the following manner in accordance with the method of H. Kondo et. al. (J. Antibiotics, Vol. 43, pp. 1533–1542, 1990).

That is, uteri taken from hogs were disrupted in 5 mM phosphate buffer by means of Polytron homogenizer, and this solution was centrifuged (100,000×g, 30 min) to separate the supernatant, thereby preparing a cytosol containing progesterone receptor. A given concentration of a test drug solution (10 μl) was added to a solution composed of 50 μl of the cytosol obtained Just above (2–3 mg protein/ml) and 40 μl of a solution of [$^3$H]-progesterone as a ligand (3.84 TBq/mM, 18.5 kBq/ml), and they were incubated in a test tube for 60 min at 4° C. to effect a reaction. Then, 100 μl of a 0.5% activated carbon solution was added to the reaction solution, and the mixture was allowed to stand for 10 min and then centrifuged (2,000×g, 10 min). The radioactivity of the supernatant was measured with a liquid scintillation counter.

Separately, the radioactivity was measured in the same manner as described above, except that no test drug was added. Further, the radioactivity was measured in the same manner as described above, except that 10 μl of Medroxyprogesterone Acetate (MPA) (10 μg/ml) was added instead of the test drug. The radioactivity with no test drug added was defined as the amount of total binding of [$^3$H]-progesterone to the cytosol, and the radioactivity with MPA added was defined as the amount of non-specific binding. The inhibition ratio was calculated from these measured values by the following equation to determine the binding inhibitory activity (IC$_{50}$).

Inhibition ratio (%) =

$$\left(1 - \frac{\text{(total binding amount with test drug added)} - \text{(non-specific binding amount)}}{\text{(total binding amount with no test drug added)} - \text{(non-specific binding amount)}}\right) \times 100$$

The compounds prepared in Examples 7a, 7b, 14a, 15, 16, 21a and 21b had inhibitory activity against progesterone receptor binding as summarized in Table 1.

TABLE 1

Inhibitory activity against progesterone receptor binding

| Example No. of compound | Inhibitory activity (IC$_{50}$) (nM) |
|---|---|
| 7a | <100 |
| 7b | <100 |
| 14a | 600 |
| 15 | <100 |
| 16 | 400 |
| 21a | 700 |
| 21b | 279 |

PREPARATION EXAMPLE

Tablets

An intimate powder mixture of the compound prepared in Example 7b, lactose, crosslinked polyvidone, and hydroxypropylmethyl cellulose was prepared and wet-granulated by a conventional method, and magnesium stearate in an amount of 0.5 mg/tablet was added thereto.

The resultant mixture was compressed by a conventional method to prepare tablets. Each tablet had the following composition.

| Compound of Example 7b | 5.0 mg |
|---|---|
| Lactose | 185 mg |
| Crosslinked polyvidone | 7.0 mg |
| Hydroxypropylmethyl cellulose | 2.5 mg |
| Magnesium stearate | 0.5 mg |
| | 200 mg |

What is claimed is:

1. A compound represented by the following formula (I) or a salt thereof:

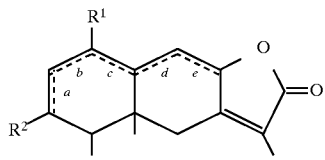

(I)

wherein
R$^1$ represents a hydrogen atom, a halogen atom, C$_1$–C$_5$ alkoxy, or phenylthio;
R$^2$ represents C$_1$–C$_5$ alkoxy or C$_2$–C$_5$ alkanoyloxy; and
---- with letters a, b, c, d, and e attached thereto are such that when b and d represent a double bond, a, c, and e represent a single bond; when b and d represent a single bond, a represents a single bond or a double bond with c and e representing a double bond where, when a represents a double bond, both R$^1$ and R$^2$ represent a hydrogen atom.

2. The compound according to claim 1, wherein b and d represent a double bond with a, c, and e representing a single bond.

3. The compound according to claim 1, wherein b and d represent a single bond, a represents a double bond, c and e represent a double bond and both R$^1$ and R$^2$ represent a hydrogen atom.

4. The compound according to claim 1, wherein b and d represent a single bond, a represents a single bond and c and e represent a double bond.

5. A pharmaceutical composition comprising as an active ingredient the compound according to any one of claims 1 to 4.

6. The pharmaceutical composition according to claim 5, which is a therapeutic or prophylactic agent for progesterone-related diseases.

7. The pharmaceutical composition according to claim 6, which is a carcinostatic agent for breast cancer or ovarian cancer, a therapeutic agent for hysteromyoma, endometriosis, meningioma, or myeloma, an abortifacient, an oral contraceptive pill, or a therapeutic or prophylactic agent for osteoporosis or climacteric disturbance.

* * * * *